(12) United States Patent
Chen et al.

(10) Patent No.: US 7,753,961 B2
(45) Date of Patent: Jul. 13, 2010

(54) THIGHBONE SHAFT

(75) Inventors: Tain-Hsiung Chen, Hsinchu (TW);
Chen-Yu Lung, Hsinchu (TW)

(73) Assignee: United Orthopedic Corporation, Hsinchu (TW)

( * ) Notice: Subject to any disclaimer, the term of this patent is extended or adjusted under 35 U.S.C. 154(b) by 0 days.

(21) Appl. No.: 11/034,942

(22) Filed: Jan. 14, 2005

(65) Prior Publication Data
US 2006/0161262 A1 Jul. 20, 2006

(51) Int. Cl.
*A61F 2/36* (2006.01)
(52) U.S. Cl. .............. 623/22.46; 623/23.24; 606/62
(58) Field of Classification Search ......... 623/2.11–2.14, 623/22.4–22.42, 22.43–22.44, 22.46, 23.24, 623/23.26, 23.27, 23.29, 23.3, 23.31, 20.36, 623/23.14, 23.15, 23.18, 23.23, 23.33, 23.35, 623/23.44, 23.46; 606/84, 85, 89, 62–63
See application file for complete search history.

(56) References Cited

U.S. PATENT DOCUMENTS

| | | | | |
|---|---|---|---|---|
| 5,163,961 A | * | 11/1992 | Harwin | 623/22.46 |
| 5,741,262 A | * | 4/1998 | Albrektsson et al. | 606/80 |
| 5,755,805 A | * | 5/1998 | Whiteside | 623/23.24 |
| 6,616,697 B2 | * | 9/2003 | Sotereanos | 623/23.26 |
| 2003/0050704 A1 | * | 3/2003 | Keynan | 623/22.12 |
| 2004/0162621 A1 | * | 8/2004 | Crofford | 623/22.43 |

FOREIGN PATENT DOCUMENTS

FR 2 705 558 A1 * 12/1994
RU 2 066 153 C1 * 9/1996

* cited by examiner

*Primary Examiner*—David H. Willse
(74) *Attorney, Agent, or Firm*—Muncy, Geissler, Olds & Lowe, PLLC

(57) ABSTRACT

A thighbone shaft has a pole and a bolt. The pole defines an inclined threaded hole therein. Tooth portions are respectively formed at opposite sides of the pole. A head is arranged on a front portion of the pole. A sleeve is provided on the head. A threaded portion is formed on the bolt and is retained in the inclined threaded hole for engaging the bolt and the pole. The thighbone shaft is assembled easily, reduces planting area and replacement cost, decreases stress force, and promotes planting fixedness.

3 Claims, 5 Drawing Sheets

THIGHBONE SHAFT

BACKGROUND OF THE INVENTION (a) Field of the Invention

The present invention relates to a thighbone shaft, and particularly to a thighbone shaft which has a pole and a bolt mounted on an inclined threaded hole in the pole and which is adapted for artificial joint or the similar.

(b) Description of the Prior Art

As disclosed in Taiwan Patent No. 89219012, a conventional artificial joint has a thighbone shaft, which is made of titanium alloy and plants into a user's thighbone. The thighbone shaft comprises:

a front portion, which shrinks gradually and is covered by an adhesion layer and a coating layer, a neck portion connecting with an end of the front portion, a sleeve portion connecting with the neck portion;

a middle portion connecting with an end of the front portion and opposite to the neck portion, and forming a rough surface;

a tail portion connecting with an end of the middle portion, and forming a polishing surface, symmetric grooves being defined in the polishing surface.

In this design, stress force put on the tail portion is reduced, thereby avoiding pain feel of thighbone side, achieving optimal planting effect, and decreasing occurrence of strain barrier. However, this design damages large area of thighbone and produces large area of wound. Moreover, the thighbone shaft is relatively large. The overall thighbone shaft has to be replaced when the thighbone shaft is worn out after long period of use. Such a thighbone shaft cannot meet users' need.

SUMMARY OF THE INVENTION

Accordingly, an object of the present invention is to provide a thighbone shaft, which has a pole, a head arranged on a front portion of the pole, and a bolt mounted on an inclined threaded hole in the pole, whereby the stress force portion of the thighbone, namely thighbone neck, remains. A thighbone neck acts as a planting point, damaging small area of the thighbone. Only thighbone and acetabulum which have worn-out cartilage need to be replaced, and therefore wound area is relatively small, size of planted thighbone shaft is reduced, stress force decreases, and convenience and utility increases.

Another object of the present invention is to provide a thighbone shaft, wherein only a head thereof need to be replaced rather than the overall thighbone shaft after long term of use, thereby reducing cost and making operation easier.

A further object of the present invention is to provide a thighbone shaft, which has tooth portions on opposite sides of the pole thereof for increasing contact area of planting and forming lock structure, thereby promoting planting fixedness.

A thighbone shaft of the present invention comprises a pole and a bolt. The pole defines an inclined threaded hole therein. Tooth portions are respectively formed at opposite sides of the pole. A head is arranged on a front portion of the pole. A sleeve is provided on a front portion of the head. The bolt forms a threaded portion for fitting in the inclined threaded hole thereby engaging the bolt with the pole. Thus, the thighbone shaft is assembled easily, simultaneously reducing planting area and replacement cost, decreasing stress force, and promoting planting fixedness.

DETAILED DESCRIPTION OF THE PREFERRED EMBODIMENTS

Figure 1:
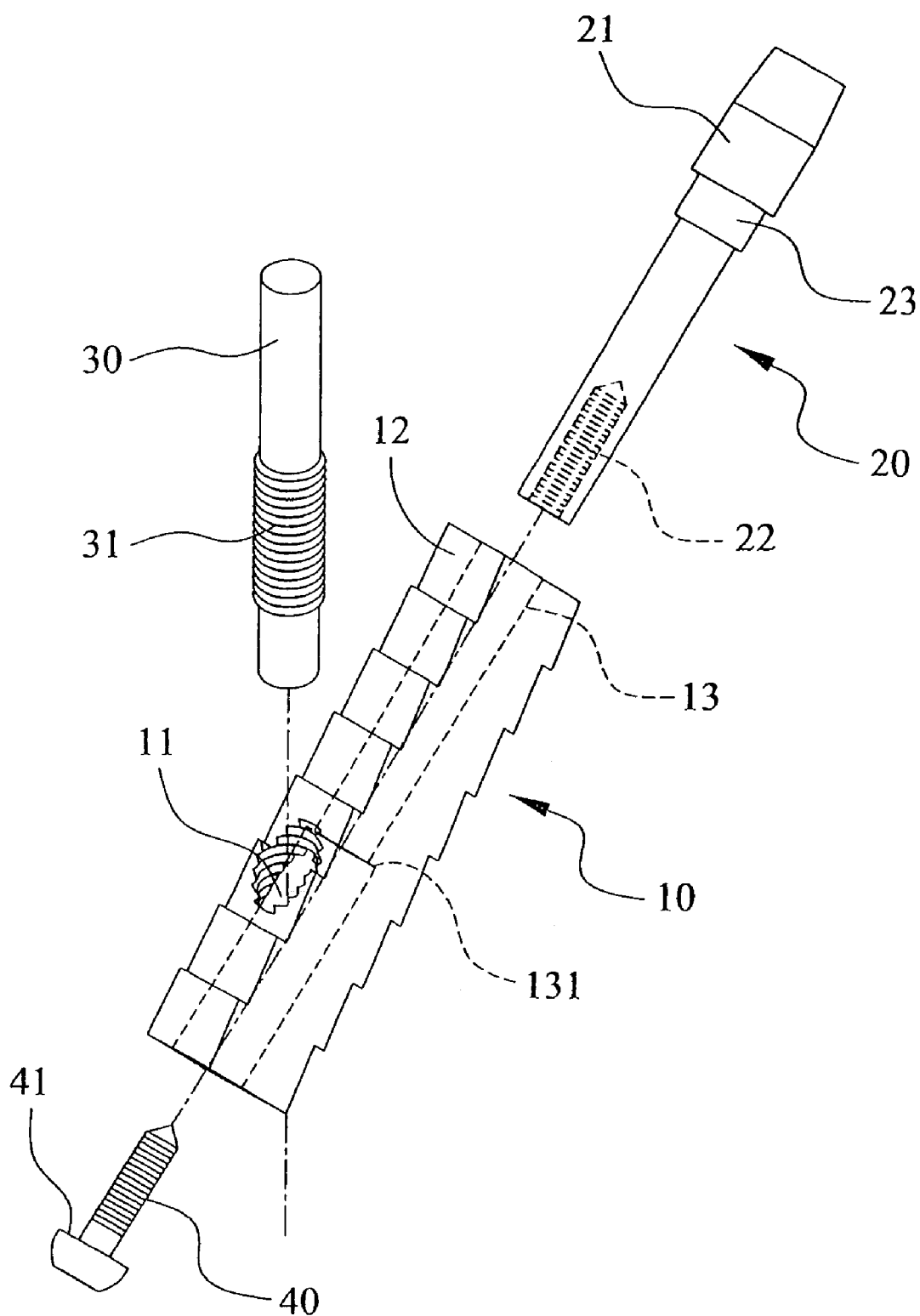
FIG. 1 is an exploded view of a first embodiment of a thighbone shaft according to the present invention.
Figure 2:
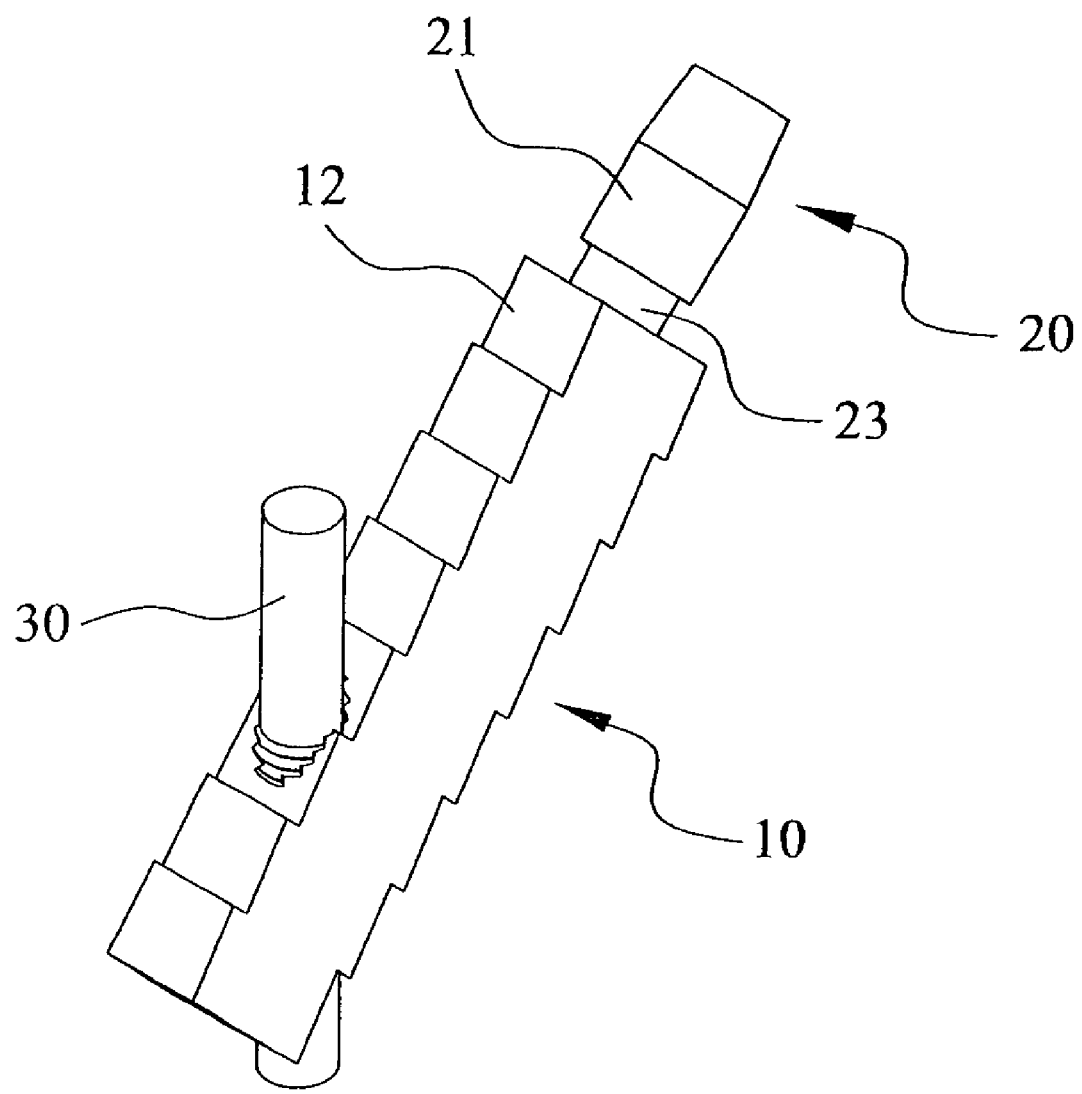
FIG. 2 is a perspective view of the thighbone shaft of FIG. 1.
Figure 3:
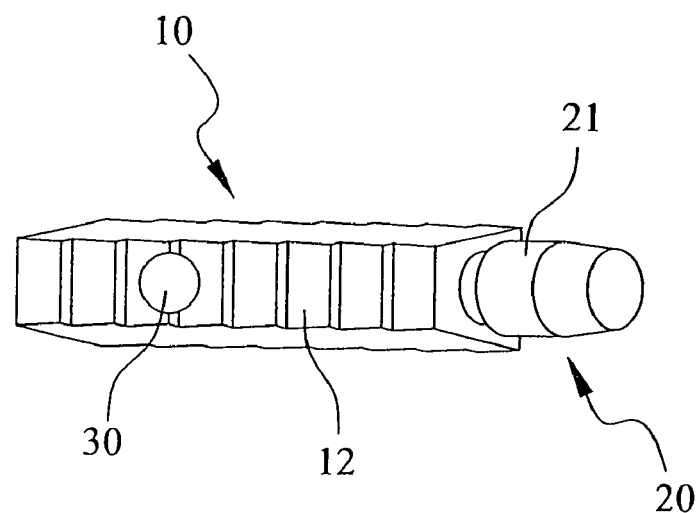
FIG. 3 shows a side of the thighbone shaft of FIG. 1.
Figure 4:
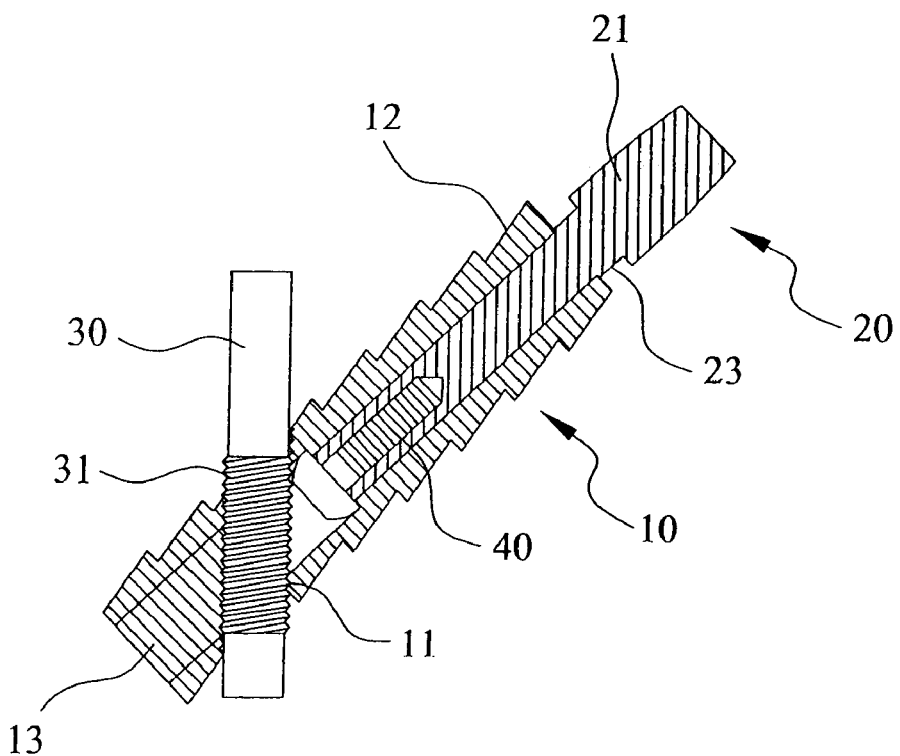
FIG. 4 is a schematically sectional view of the thighbone shaft of FIG. 1.

With reference to FIGS. 1 to 4, a thighbone shaft of a first embodiment of the present invention comprises a pole 10, a head 20 mounted on the pole 10, and a separate bolt 30. The pole 10 defines an inclined threaded hole 11 therein. Tooth portions 12 are respectively formed at opposite sides of the pole 10. A through hole 13 is longitudinally defined through a center of the pole 10. A step 131 is formed in the through hole 13.

The head 20 has a rear end fixed on the through hole 13, and a front end beyond the pole 10. The head 20 defines a positioning hole 22 in the rear end thereof for engaging firmly with a fixing element 40. The fixing element 40 forms a shoulder 41 for abutting with the step 131 in the through hole 13. A sleeve 21 is provided on the front end of the head 20. The head 20 forms a projection 23 at rear of the sleeve 21 for abutting a front surface of the pole 10.

The bolt 30 forms a threaded portion 31 for fitting in the inclined threaded hole 11 of the pole 10, thereby engaging the bolt 30 with the pole 10.

Figure 5:
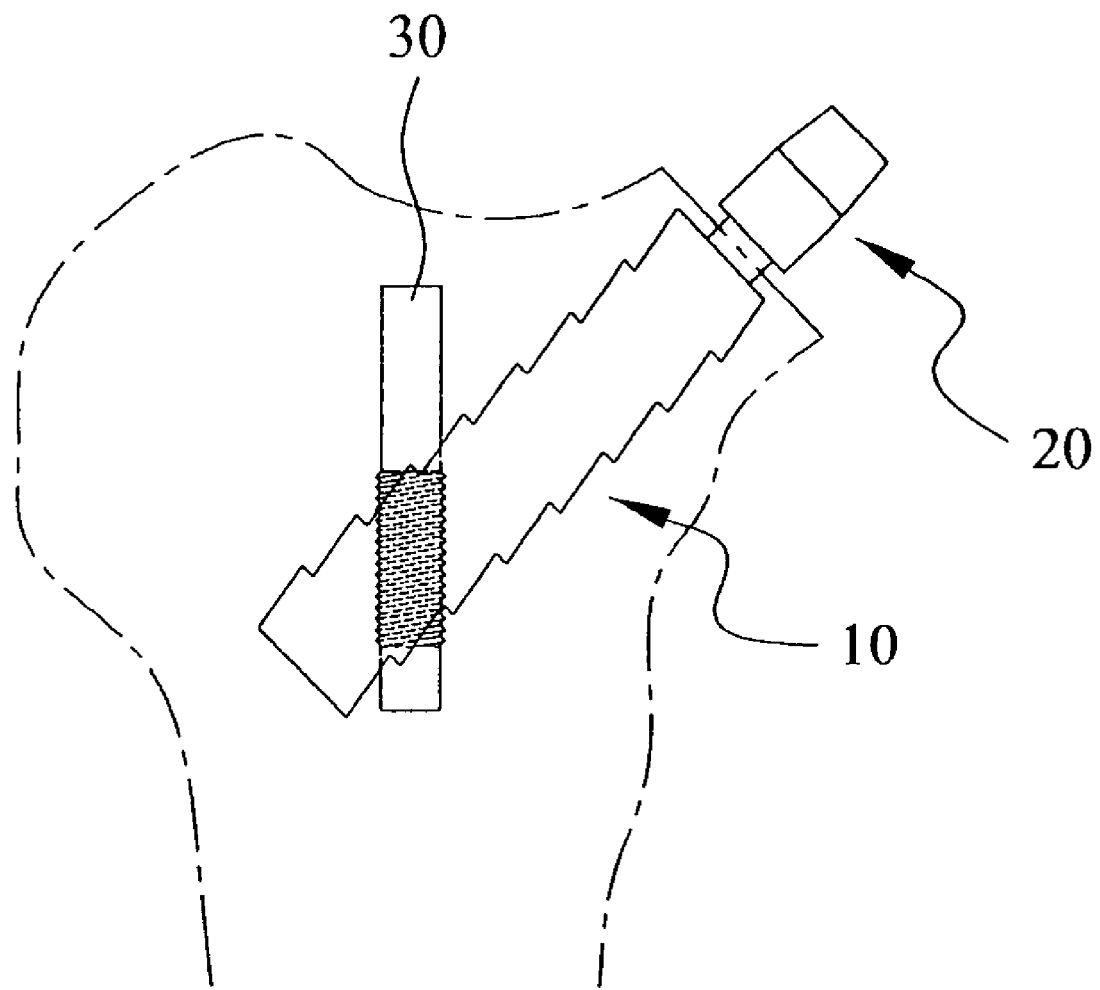
FIG. 5 is an assembled view of the thighbone of FIG. 1, wherein the thighbone shaft is in use.

Further referring to FIG. 5, the head 20 is fixed on the through hole 13 of the pole 10. The projection 23 abuts a front surface of the pole 10. The fixing element 40 is fitted in a rear portion of the through hole 13 and is firmly retained on the positioning hole 22. The shoulder 41 of the fixing element 40 abuts against the step 131 in the through hole 13, whereby the head 20 is retained in the through hole 13 reliably. The threaded portion 31 of the bolt 30 engages with the inclined threaded hole 11 to connect the pole 10 and the bolt 30, resulting in decrease of strain force. Thus, the stress force portion of the thighbone, namely a thighbone neck, remains. A thighbone neck acts as a planting point, damaging small area of the thighbone. Only thighbone and acetabulum which have worn-out cartilage need to be replaced, and therefore wound area is relatively small and size of planted thighbone shaft is reduced. After long term of use, once the head 20 is worn out, only the head 20 need to be replaced rather than the overall thighbone shaft, reducing cost and making operation easier.

The tooth portions 12 on the pole 10 increase contact area of planting and form lock structure, promoting planting fixedness and achieving optimal planting effect.

Figure 6:
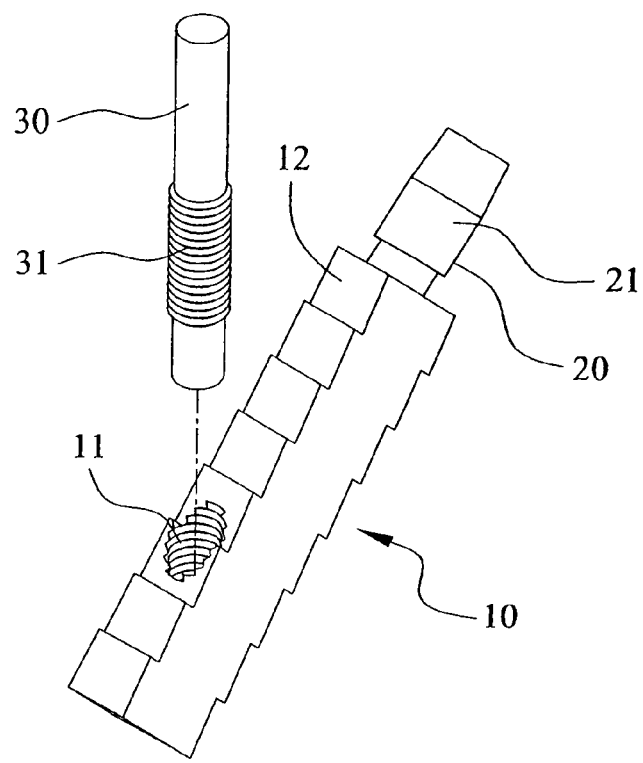
FIG. 6 is an exploded view of a second embodiment of the thighbone shaft of the present invention.
Figure 7:
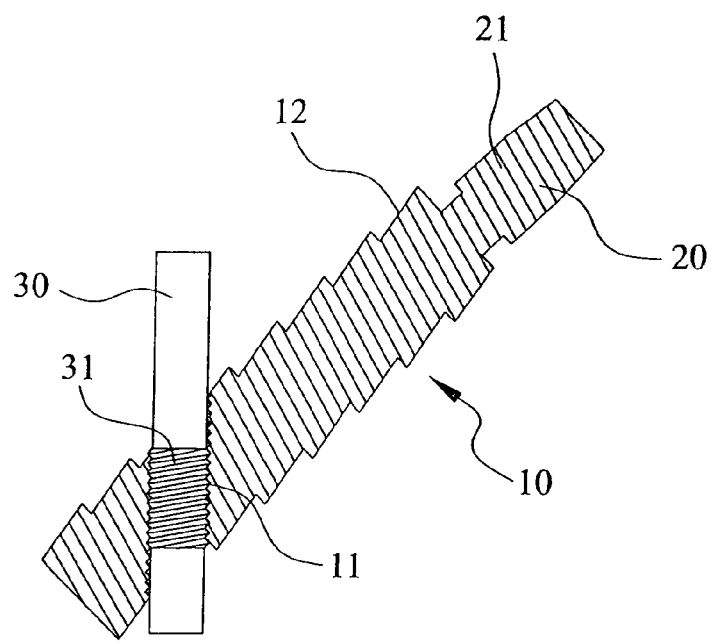
FIG. 7 is a sectional view of the thighbone shaft of FIG. 6.

Referring to FIGS. 6 and 7, according to a second embodiment of the present invention, the pole 10 defines an inclined threaded hole 11 therein. Tooth portions 12 are respectively formed at opposite sides of the pole 10. The head 20 and the pole 10 are integrally formed. A sleeve 21 is provided on the front end of the head 20. The bolt 30 forms a threaded portion 31 for fitting in the inclined threaded hole 11 of the pole 10, thereby engaging the bolt 30 with the pole 10. This assembly process is easy. The present invention reduces planting area and stress force and increasing planting fixedness. So it is rather useful and convenient.

It is understood that the invention may be embodied in other forms without departing from the spirit thereof. Thus, the present examples and embodiments are to be considered in all respects as illustrative and not restrictive, and the invention is not to be limited to the details given herein.

What is claimed is:

1. A thighbone shaft comprising:
   a) a pole having:
      i) an inclined threaded hole extending through an outer periphery thereof; and
      ii) a plurality of steps located on opposing sides of the outer periphery thereof, each of the plurality of steps is offset relative to an adjacent step forming a continuous stepped surface;
   b) a head having:
      i) a projection having a first end connected to an end of the pole; and
      ii) a sleeve located on a second end of the projection;
   c) a bolt inserted into the inclined threaded hole and having a threaded portion threadedly connected to the inclined threaded hole; and
   d) a fixing element having a shoulder, the pole has a through hole extending axially through a length thereof, the through hole of the pole has a step, the projection of the head has a positioning hole located on the first end and the first end is inserted into the through hole, the fixing element is inserted into the through hole and connected to the positioning hole, and the shoulder of the fixing element engaging the step of the through hole.

2. The thighbone shaft according to claim 1, wherein the sleeve is spaced apart from the pole by a portion of the projection.

3. The thighbone shaft according to claim 1, wherein the threaded portion of the bolt is located on a middle portion thereof, two ends of the bolt protruding from the opposing sides of the pole.

* * * * *